United States Patent [19]

Cosentino et al.

[11] Patent Number: 4,721,123

[45] Date of Patent: Jan. 26, 1988

[54] CATHETER REPROCESSING SYSTEM

[75] Inventors: Louis C. Cosentino, Wayzata; Daniel A. Baker, Minnetonka; Edward J. Mikolajczyk, Minneapolis; Russel L. Hoeker, Maple Grove; Jo-Ann B. Maltais, Minneapolis, all of Minn.

[73] Assignee: Minntech Corporation, Minneapolis, Minn.

[21] Appl. No.: 922,205

[22] Filed: Oct. 23, 1986

[51] Int. Cl.⁴ ............................ B08B 3/04; B08B 9/00; B08B 11/02
[52] U.S. Cl. ............................... 134/57 R; 73/37; 134/113; 604/97; 604/171
[58] Field of Search ............... 134/56 R, 57 R, 113; 604/97, 99, 171; 73/37

[56] References Cited

U.S. PATENT DOCUMENTS

| | | | |
|---|---|---|---|
| 3,697,418 | 10/1972 | Johnson | 210/195 X |
| 4,166,031 | 8/1979 | Hardy | 210/22 A |
| 4,243,033 | 1/1981 | DeCaprio et al. | 604/171 X |
| 4,332,264 | 6/1982 | Gortz etal. | 134/57 R |
| 4,517,081 | 5/1985 | Amiot et al. | 210/85 |
| 4,654,027 | 3/1987 | Dragan et al. | 604/99 |

OTHER PUBLICATIONS

1985 Annual Report for Renal Systems, Inc., (now Minntech Corporation).
Corporate Report Minnesota, "Plumbing the Limits of Cradiovascular Technology" by Jim Thornton, Jan. 1987, pp. 86, 87, 116 & 118.
Instruction manual headed "MA-DE Inc." for MA-DE A100 Automatic Re-Use Machine and Catridge, by Barry Mason, Oct. 4, 1974, pp. 1–9.
United Medical Products, Inc., "How Clean is Clean?", date unknown, pp. 1–7.
Article "Multiple Use of Dialyzers is Now Practical Reality", authors Gortz, Huson, and MacIntyre, is patent pending, refering to FDA contract of Jun. 1980.
Cobe Laboratories, Inc., 1972, T.M. Life Science Systems, Inc., pp. 1–3.

Primary Examiner—Philip R. Coe
Attorney, Agent, or Firm—Vidas & Arrett

[57] ABSTRACT

A machine for reprocessing catheters of the type having a double lumen, one of which leads to a balloon. A used catheter is sealed within a cassette which in turn is connected by multiple ports to a cleaning side of the machine. Cleaning solution is flushed through the inside and outside of the catheter. The balloon integrity is tested by adding step wise volume additions and monitoring the pressure. The data generated is compared to a standard curve for new catheters. The cleaned, sterile catheter is then rinsed to remove all traces of sterilant. Sterile saline is alternatively flushed through the cassette and catheter. The balloon is again tested for leaks. No portion of the rinse side of the machine requires sterilizing except for the disposable tubing set and saline source. The rinsed, clean and sterile catheter is removed from the cassette for reuse.

16 Claims, 17 Drawing Figures

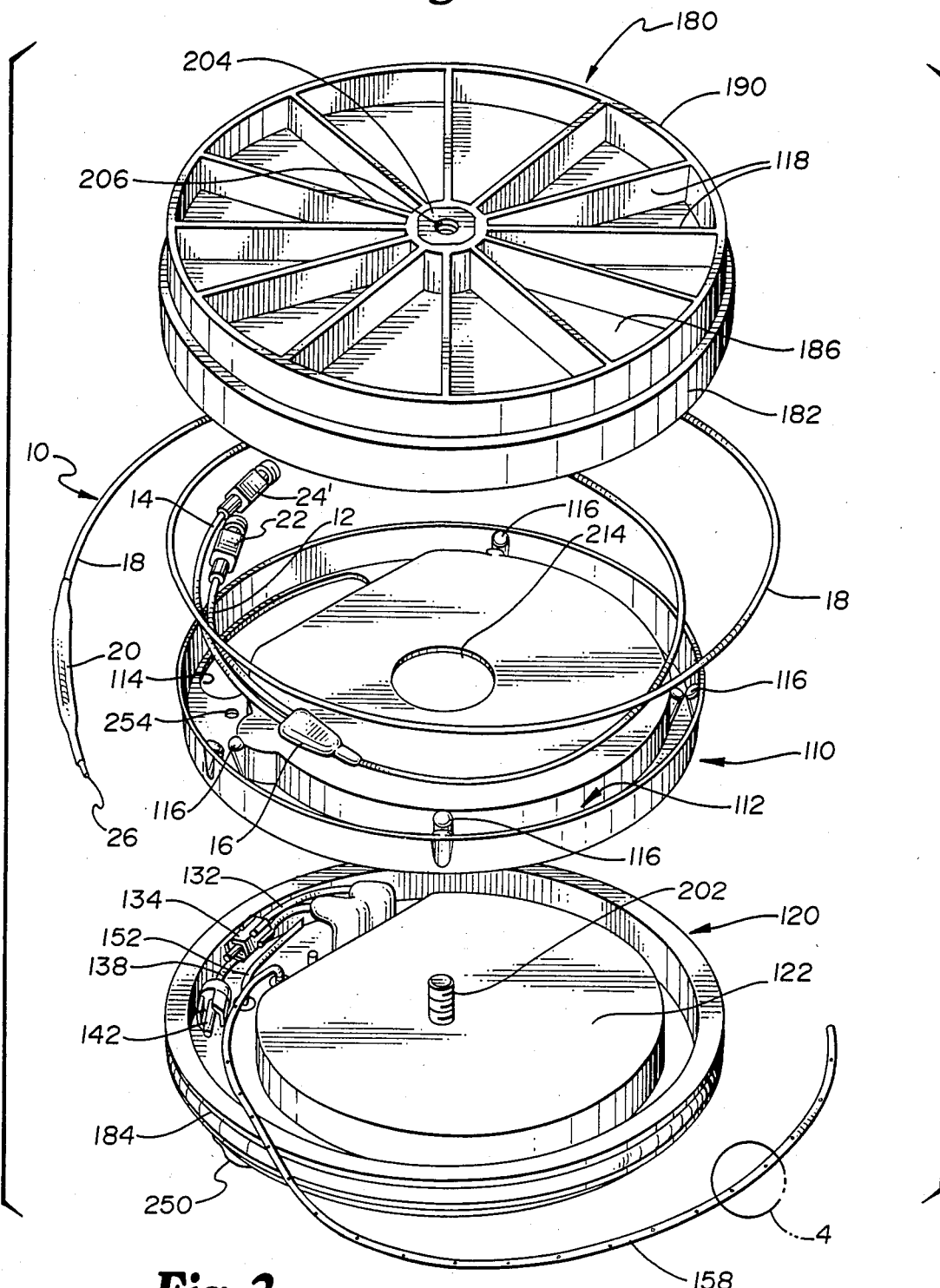
*Fig. 2*
*Fig. 3*
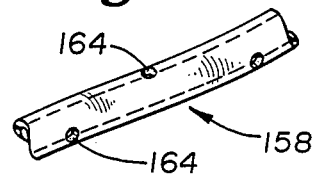

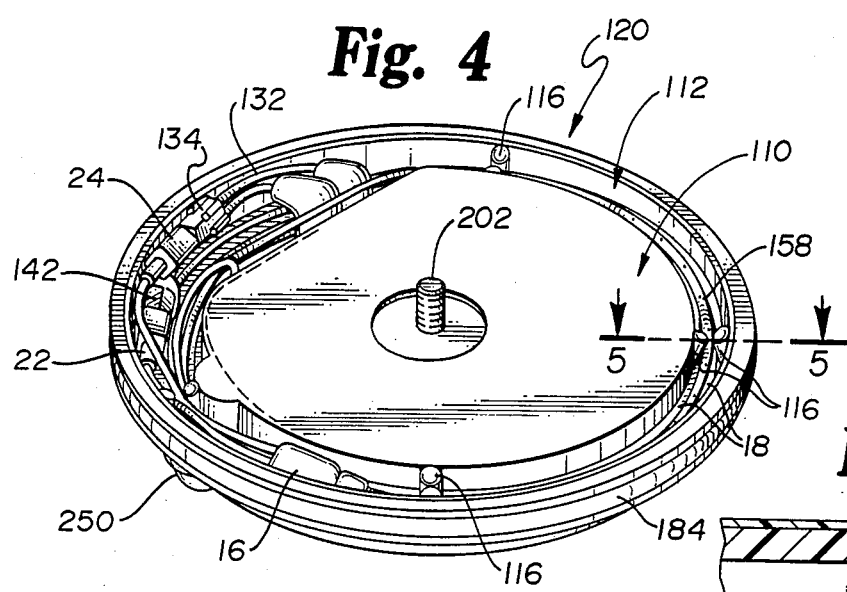
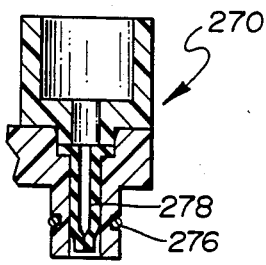
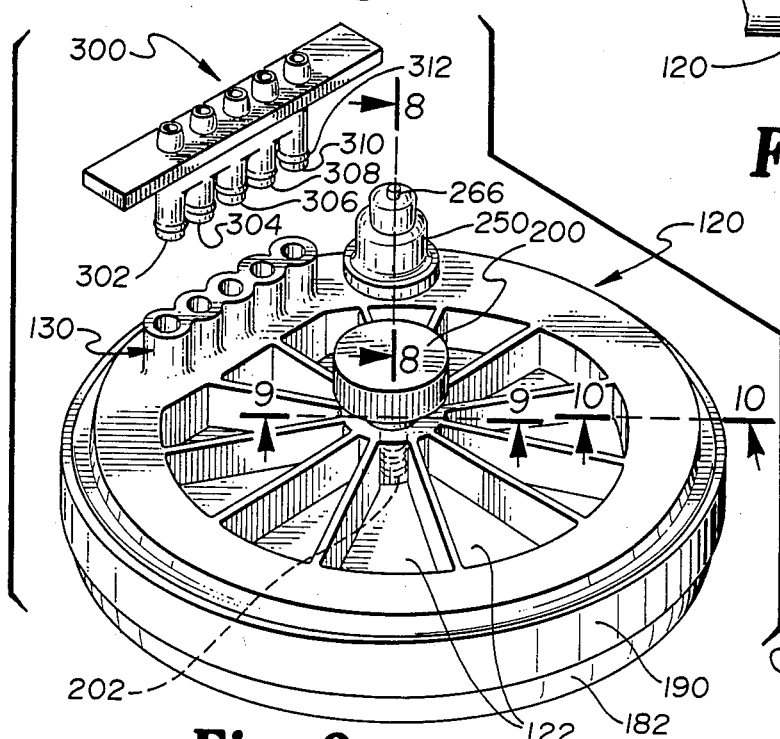
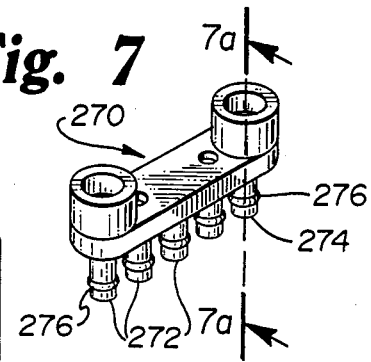
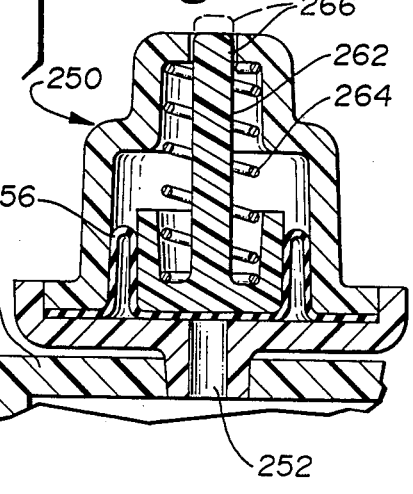
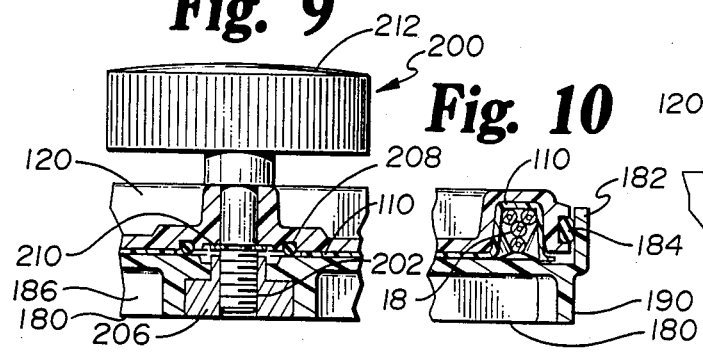
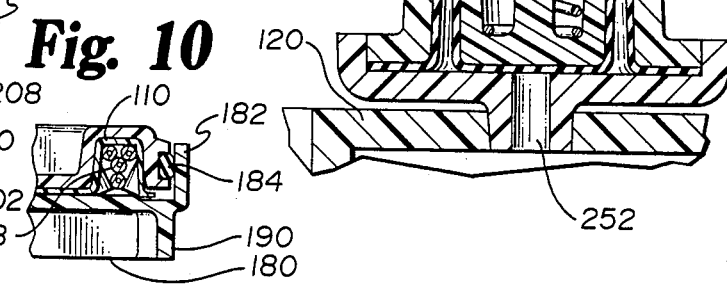

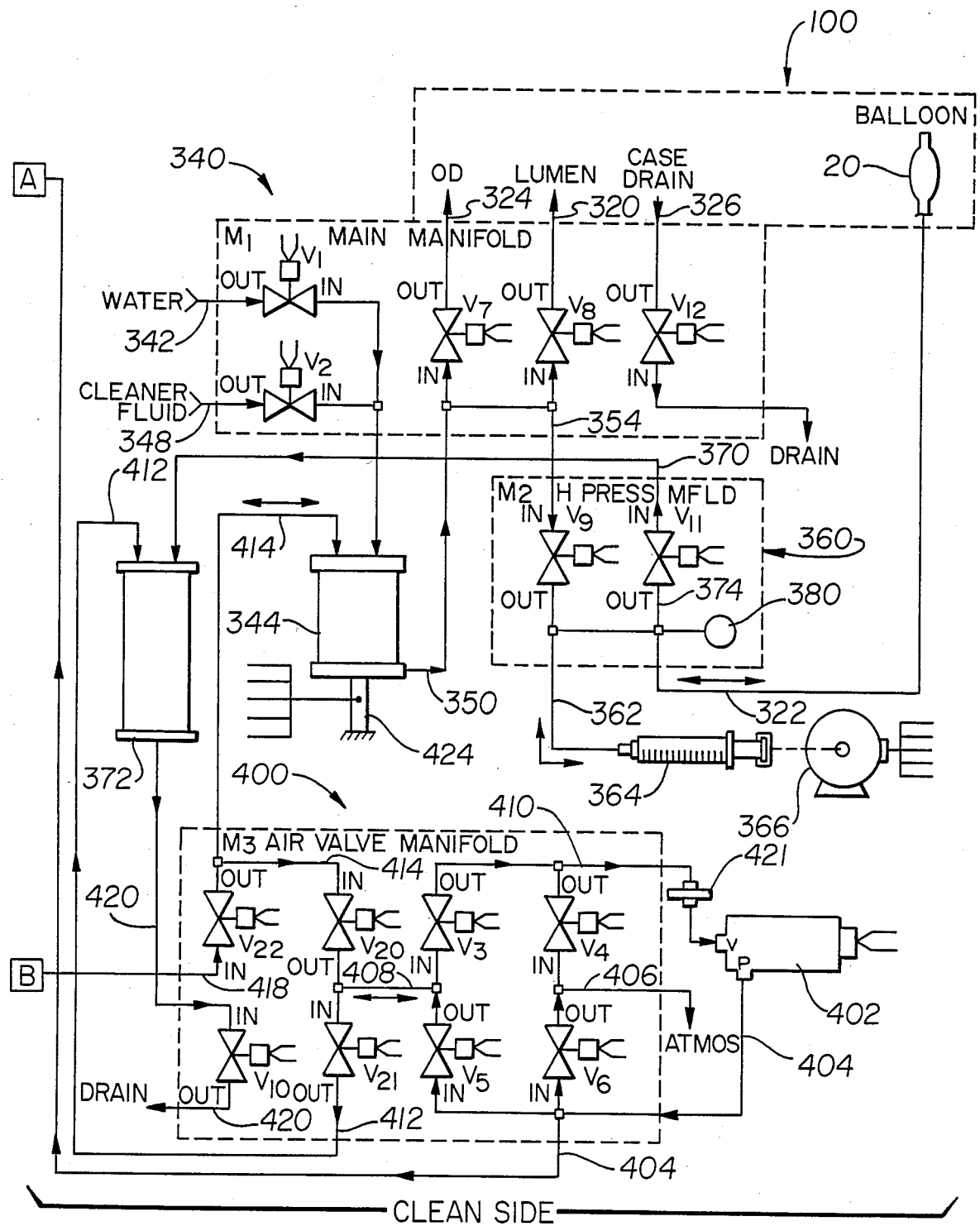

CATHETER REPROCESSING SYSTEM

FIELD OF THE INVENTION

This invention generally relates to a method and an apparatus for reprocessing catheters of the type having an inflatable balloon. More specifically, the invention relates to methods and an apparatus for cleaning catheters and for evaluating the condition of the catheter.

BACKGROUND OF THE INVENTION

Balloon tipped catheters have been developed in recent years to perform a variety of delicate operations within a living body. For example, Percutaneous Transuminal Coronary Angioplasty (PTCA) has been developed to open partially blocked coronary arteries. PTCA is performed by inserting a balloon tipped catheter into the blocked artery. When filled with fluid, the balloon opens the blocked artery. PTCA is often an alternative to coronary artery bypass surgery. The number of PTCA procedures is expected to increase from about 28,000 in 1983 to more than 75,000 in 1988.

The cost of catheters represents a significant portion of the overall cost of the procedures. PTCA catheters are quite expensive, costing several hundreds of dollars.

The reuse of such catheters would be a great help in controlling the spiraling cost of procedures utilizing catheters. Manual reprocessing of PTCA catheters has provided a limited means for reuse in catheters. Unfortunately, manual reprocessing is very prone to human error in that the sterility of manual reprocessed catheters is not assured as compared to new catheters. Also, manual systems for testing the catheter balloons are exceedingly difficult to control and may actually cause damage to the balloon. Additionally, manual systems fail to provide the necessary identification, monitoring, control and versatility required to produce a safe, efficient and practical catheter reprocessing system.

Allegedly, some manual reprocessing of balloon-tipped Catheters has taken place outside the United States.

BRIEF SUMMARY OF THE INVENTION

The invention includes a computer controlled system having separate cleaning and rinsing units. A used catheter is placed within a cassette which in turn is connected to fluid lines of the cleaning unit. The computer stores information on the catheter as to manufacturer, model and serial number. The identity of the particular catheter is recorded to compare against manufacturers standards and to provide a use record.

Hydraulics within the system are controlled by the computer. The main reservoir for the cleaner/sterilant (hereinafter simply referred to as "cleaner") is filled and pressure is applied to force cleaner into the cassette and inside the lumens and balloon. The balloon is evacuated by a vacuum source and is then filled with cleaner to about 50% of its volume. This aspiration and filling step is repeated, preferably about 24 times.

The balloon is then tested at its maximum operating pressure. The balloon is evacuated and a stepper motor drives a syringe pump to deliver set volumes of cleaner per step. A pressure transducer records the pressure at the balloon with each volume increment. The data is fed to the computer whose program compares the pressure/volume curve to the standard pressure/volume curve for new catheters of the same model. A balloon which is blocked, leaks or is stretched will fail the comparison and further reprocessing will be cancelled. A record of the cancellation is stored under the serial number of the catheter.

If the balloon passes, it is depressurized but left filled with cleaner.

The other lumen of the catheter is flushed with a preselected volume of cleaner as measured by a load cell on the main reservoir. The computer monitors this cleaning and if the required volume does not flow through, a blockage is indicated which cancels reprocessing.

Cleaner is also flushed through the outside of the catheter. The cassette is filled with sterilant and is capped. Low pressure is applied to the capped cassette.

A visual pressure indicator provides an indication of whether the cassette has leaked after pressurizing. The catheter within the cassette is then stored for between about 11 hours and two weeks to ensure that the cleaner has thoroughly sterilized the catheter. The computer stores the data received on the catheter on a disk and preferably prints a label to be affixed to the cassette.

The sterile, clean catheter within the cassette is then loaded onto the rinsing unit side of the system. A sterile tubing set delivers sterile saline solution to the cassette to rinse the cleaning solution from the catheter and cassette.

BRIEF DESCRIPTION OF THE DRAWINGS

The detailed description of the invention, including its preferred embodiment, is hereinafter described with specific reference being made to the drawings in which:

FIG. 2 is an exploded pictorial view of the elements of FIG. 1 inverted and slightly rearranged to show details of construction;

FIG. 3 is a partial pictorial view greatly enlarged taken from the area indicated at 3 of FIG. 2;

FIG. 4 is a pictorial view of part of the inventive cassette with elements assembled preparatory to cleansing process and with the lower half of the cassette omitted from this view;

FIG. 5 is a greatly enlarged cross section taken along line 5—5 of FIG. 4;

FIG. 6 is a pictorial view of the fully assembled cassette with a processor interface connector exploded therefrom in the same figure;

FIG. 7 is a pictorial view of the plug;

FIG. 7a is a cross section taken along line 7a–7a of FIG. 7 and greatly enlarged therefrom;

FIG. 8 is a cross sectional detail taken along line 8—8 of FIG. 6 and greatly enlarged therefrom;

FIG. 9 is a section taken along line 9—9 of FIG. 6;

FIG. 10 is a section taken along line 10—10 of FIG. 6;

DETAILED DESCRIPTION OF THE INVENTION

The inventive catheter reprocessing system for cleaning and sterilizing used catheters requires a catheter holding cassette which allows all of the cleaning, testing and rinsing steps to be conducted and which will insure that sterility can be maintained. The catheter holding cassette of the invention is shown in FIGS. 1–10.

Figure 1:
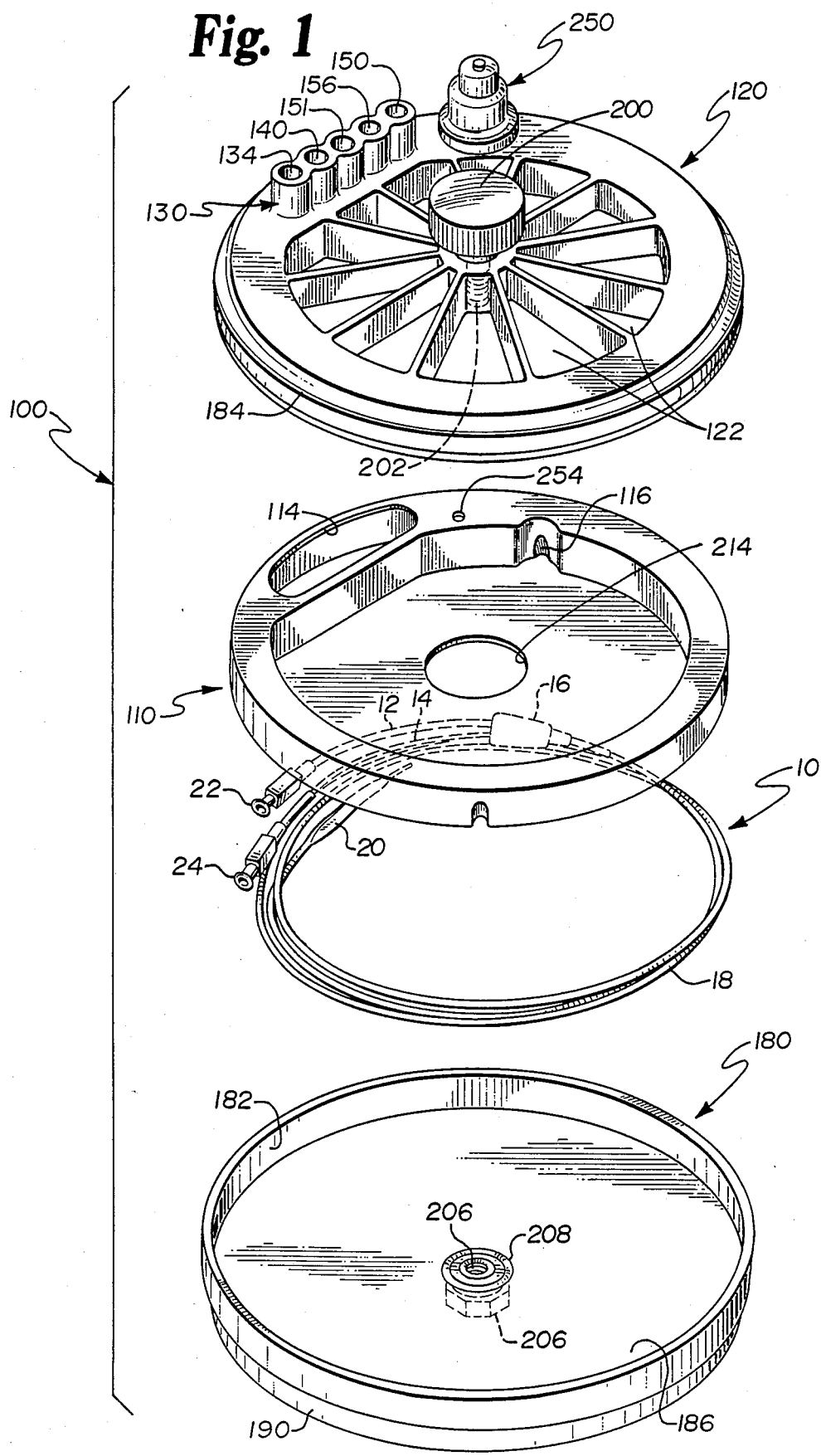
FIG. 1 is an exploded pictorial view of the cassette of the invention along with a typical balloon catheter.

For ease of understanding, a typical catheter to be reprocessed and reused is shown in FIGS. 1 and 2. Catheter 10 includes a pair of tubes 12 and 14 which meet at bifurcating hub 16 and are encased together in a "piggy-back" style along length 18. Near the end of length 18, tube 12 feeds into balloon 20 which encircles tube 14. The entire catheter is usually on the order of about one and a half meters in length. The balloon 20 is typically about 25 mm long and may be inflated to a maximum of 90 pounds per square inch (psi). The high pressure and diameter of the balloon are used in PTCA to open blocked arteries.

Catheter 10 includes a lumen luer lock connector 22 at the end of tube 12 and a luer lock connector 24 at the end of tube 14. The other end of tube 14 has an outlet 26. During use, catheter 10 becomes contaminated by blood and body fluids. Proteins may adhere to both the exterior and interior of the tubes. Sterilizing the catheter is insufficient to make the catheter reusable since the presence of proteins and other contaminants represent antigens which may be life threatening to another individual.

Catheter Preparation

Used catheters should be filled with water or saline immediately after use and stored wet. Catheters are preferably reprocessed within 2 hours of use. The catheter should be inspected visually for signs of damage and discarded if damaged. The guide wire of the catheter and any peripheral connectors attached to luer locks 22 and 24 should be removed.

The catheter is then ready to insert into cassette 100. Cassette 100 includes a transparent plastic tray 110 which defines a slot 112 into which a catheter 10 may be coiled as shown in FIGS. 1 and 2. A pass through hole 114 allows physical connections of luer locks 22, 24 to be made. A plurality of molded lumen holders 116 which act as pinch points prevents the coiled catheter from falling out of the tray. See FIG. 5.

Catheter 10 in tray 110 is then loaded onto the upper half 120 of cassette 100. As shown in FIGS. 1, 2 and 4, upper half 120 of the cassette is a circular, plastic tray defining an upper diaphragm 122 which is preferably strengthened by reinforcement webs 124. A fluid receptacle 130 provides a plurality of ports which pass into the inside of the complete cassette 100. On the inside, a plurality of lines lead from each part of the fluid receptacle. Line 132 leads from lumen port 134 and includes a connector 134 which connects to catheter lumen luer lock 24. Line 138 leads from balloon port 140 and includes connection 142 for attachment to catheter balloon luer lock 22. Drain port 150 is connected to line 152 which drains the cassette. Port 156 is connected to line 158 which, as shown in FIGS. 2 and 3, extends along the trough 160 of upper half 120. Line 158 includes a plurality of holes 164 which alternate and cross the axis of the line at regular intervals. Line 158 functions like a "soaker hose" to supply fluid along trough 160. As shown, line 158 preferably extends along nearly the circumference of trough 160.

Tray 110 is positioned such that slot 112 is fitted into trough 160. Lines 158, 152, 138 and 132 are fed through hole 114 in tray 110. Luer lock 24 is fitted to connector 134 and luer lock 22 is fitted to connector 142. FIG. 5 shows that the catheter and soaker line 158 are held adjacent each other within slot 112 of tray 110.

The lower half 180 of cassette 100 is also formed of transparent plastic and mates with upper half 120 such that seal rim 182 is sealed against rubber ring seal 184. Lower half 180 includes a lower diaphragm 186 and preferably, reinforcement ribs 188 connected to reinforcement ring 190. Together, upper half 120 and lower half 180 define a circular trough in which the coiled cassette may be placed.

Lower half 180 is connected to upper half 120 by a clamp 200 consisting of threaded stud 202 and clamp nut 204. Stud 202 is threaded into threaded hole 206. An o-ring 208 provides the seal at the clamp connection. As shown in FIG. 9, a snap ring retainer 210 holds stud 202 and knob 212 to upper half 120. FIG. 10 shows the seal achieved between upper half 120 and lower half 180 when clamp is securely tightened. Note that tray 110 includes an opening 214 through which stud 202 passes.

As shown in FIGS. 1, 6 and 8, cassette 100 includes a pressure indicator 250 for providing a visual indication that the cassette interior is under pressure. Indicator 250 penetrates the upper half 120 as shown. Lumen 252 is in line with opening 254 in tray 110 such that pressure within slot 112 may be transmitted through lumen 252. Lumen 252 is sealed by rubber diaphragm 256. Body 260 of indicator 250 holds a plunger 262 and compression spring 264 in position against diaphragm 256. When pressure is increased within slot 112 of the cassette, it is exerted against diaphragm 256 compressing spring 264. This in turn causes end 266 of plunger 262 to project above body 260.

Plug 270 as shown in FIGS. 7 and 7a may be fitted into each of the parts of fluid receptacle 130 so as to seal off the ports. Plug 270 includes four blank male fittings 272 and one active valve fitting 274. Fittings 272 and 274 include o-ring seals 276 to seal the ports. Valve fitting 274 includes a duck bill valve 278 which is normally closed until penetrated by a syringe needle. When plug 270 is connected to receptacle 130, cassette 100 is fully sealed.

Reprocessor

Figure 11:
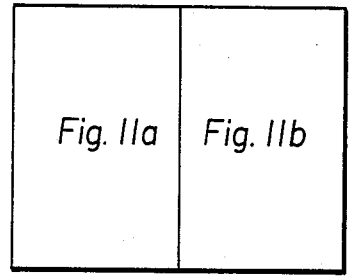
FIG. 11 consisting of FIG. 11a and FIG. 11b, is a physical layout diagram of the processor.
Figure 12:
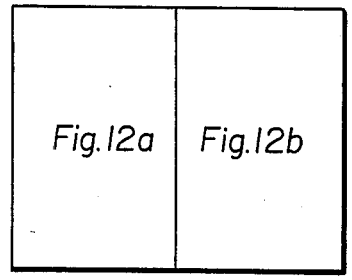
FIG. 12 consisting of FIG. 12a and FIG. 12b, is a mechanical function diagram of the processor.

As shown in FIGS. 11 and 12, the cassette 100 with a catheter 10 loaded is attached to a reprocessing machine which includes a cleaning/sterilizing side and a rinse side.

On the cleaning/sterilizing side (hereinafter "cleaning side") a cassette is connected to a port interface manifold 300 which has fittings 302, 304, 306, 308 and 310, each having an o-ring seal 312. The fittings of manifold 300 are connected to lumen tube 320, balloon tube 322, catheter exterior wash tube 324 and drain tube 326. Fitting 306 is a blank.

Figure 11A:
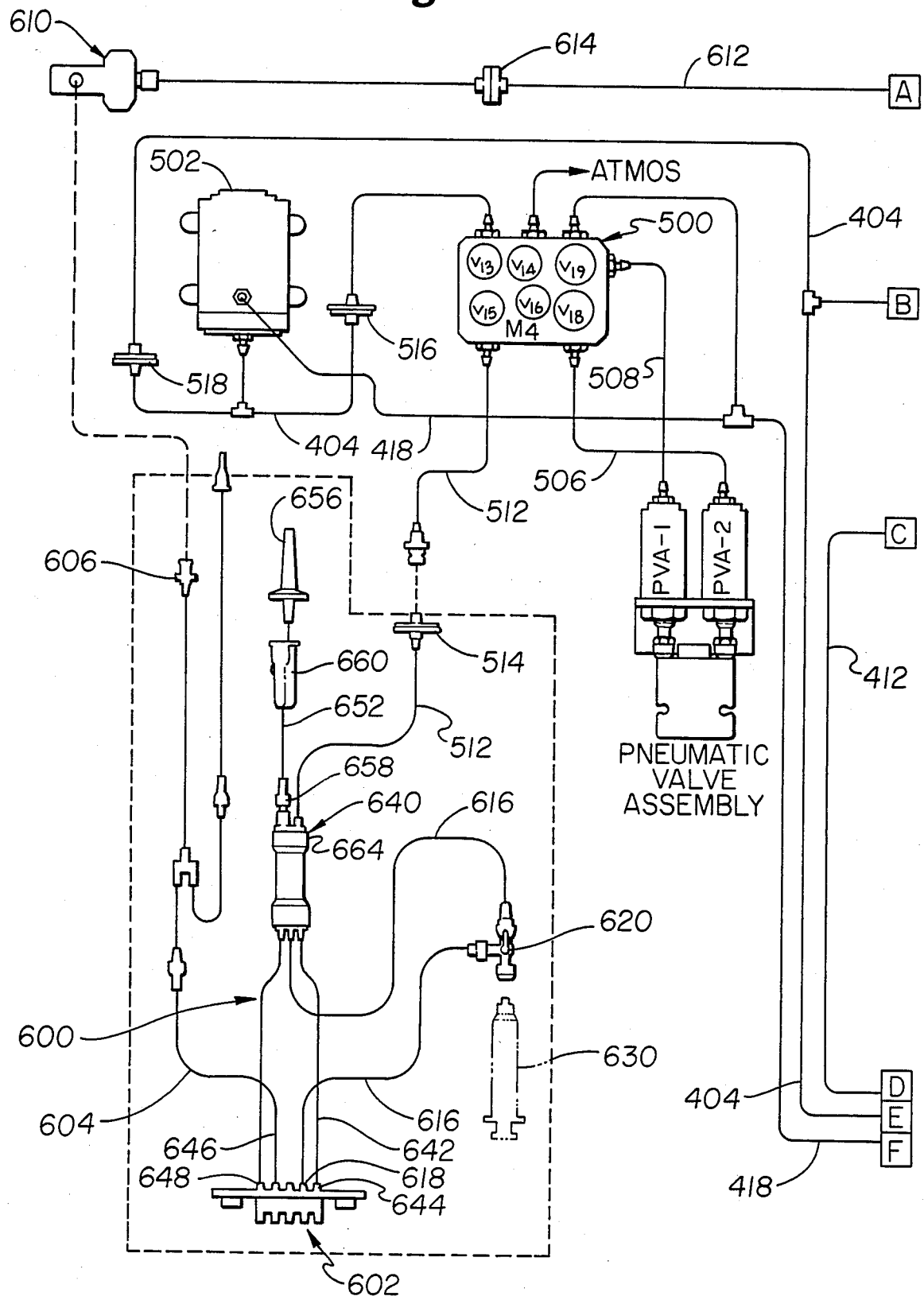
Figure 11B:
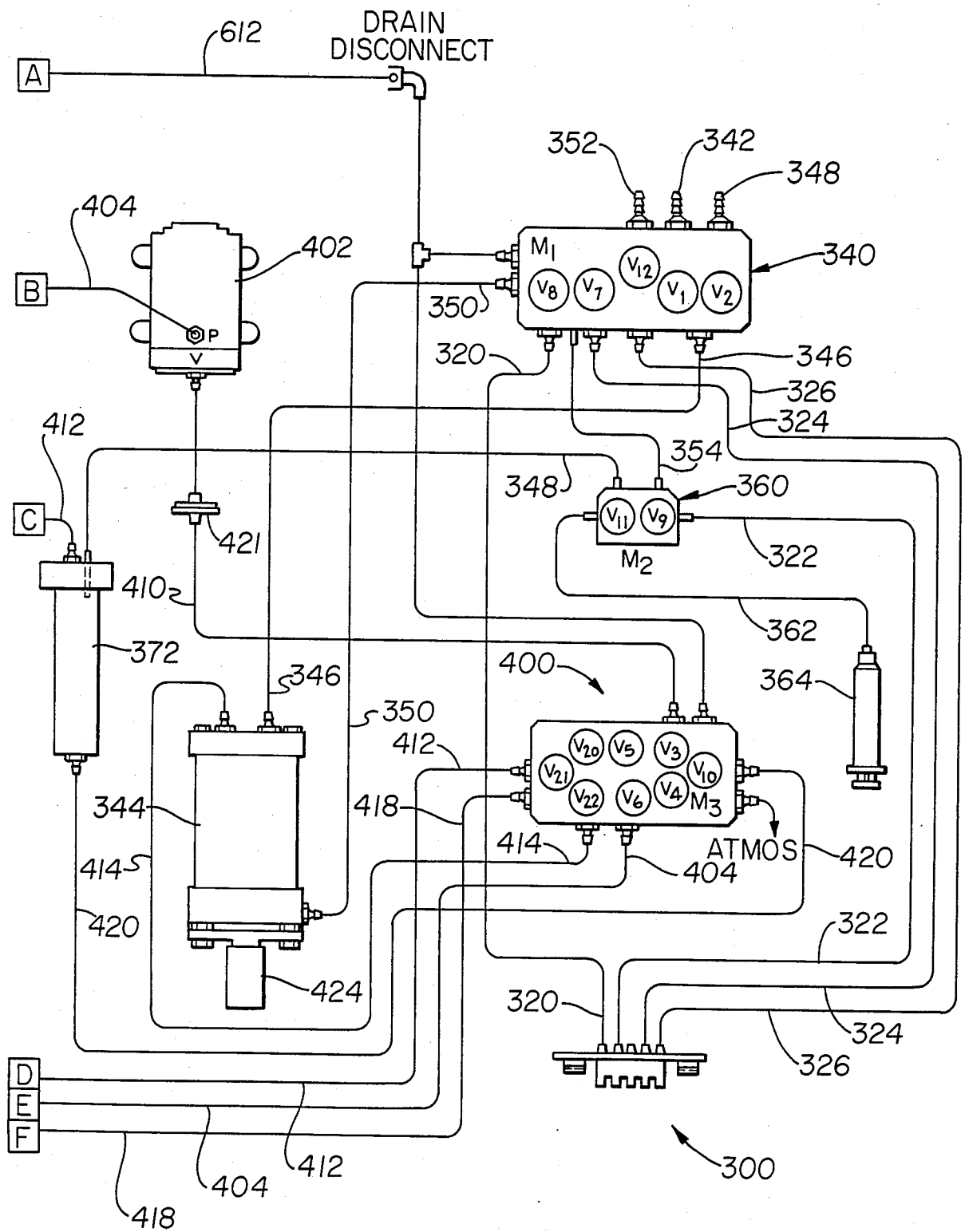
Figure 12A:
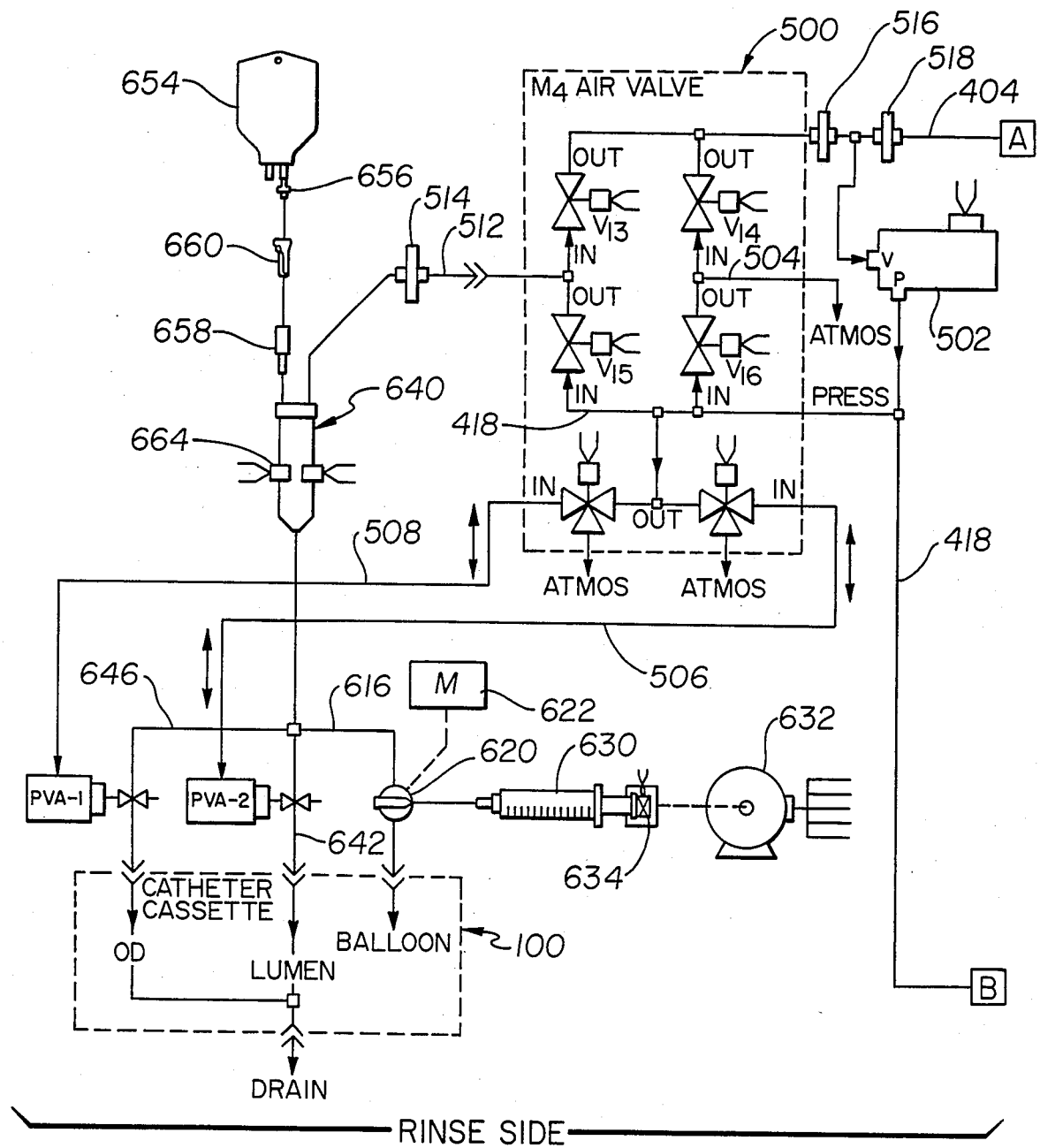

Tubes 320, 322, 324 and 326 lead to main manifold 340. As best shown in FIGS. 11b and 12b, manifold 340 includes five solenoid controlled, normally closed valves $V_1$, $V_2$, $V_7$, $V_8$, and $V_{12}$. All valves referred to herein are solenoid controlled and are normally closed with the exception of valves PVA-1 and PVA-2. Valve $V_1$ is connected to a source of diluent or water through line 342 and controls the flow of water to main tank 344 through line 346. The sterilizing/cleaning fluid (hereinafter "cleaner fluid") is fed from the cleaner fluid source through line 348 to line 346. Valve $V_2$ controls the flow of cleaner to tank 344.

Valve $V_7$ controls the flow of liquids from tank 344 to tube 324 through line 350. Valve $V_{12}$ controls flow through line 352 which is connected to a drain and to drain tube 326. Valve $V_8$ controls fluid flow to the lumen of catheter 10 through line 354. Line 354 is in direct connection with tank 344 through line 350.

High pressure manifold 360 includes a pair of valves. Valve $V_9$ controls flow through line 354 and to line 362 and line 322 which is connected to a syringe pump 364. Pump 364 is driven by stepper motor 366, which may be on Airpax model 9 2411P2. The stepper motor drives a plunger of the syringe forward in discrete steps such that each step represents a known volume. Valve $V_{11}$ controls flow through line 370 from a vacuum tank 372 and line 374 which is connected to balloon tube 322. Line 374 is directly connected to line 362 and to a pressure transducer 380 which reads pressure in line 374. When pressure is applied to balloon 20 through lines 362 and 322, the pressure transducer measures the pressure applied. With each step of the stepper motor, pressure is checked which results in data for a pressure/volume curve which is compared against a standard pressure/volume curve according to the specifications of the particular catheter model.

A cleaning side air valve manifold 400 is connected in series to a rinse side air valve manifold 500 and to vacuum tank 372 and main tank 344.

Air valve manifold 400 include eight valves which direct the output from a pump 402. Pump 402 may be a motor driven pump such as the type manufactured by Medo USA, Inc. of Wooddale, Ill., under its model MEDO V1005. The pressure side of pump 402 is connected to line 404 which leads to valve $V_5$, $V_6$, and to valves $V_{13}$ and $V_{14}$ of manifold 500. Line 404 is also connected to the vacuum side of a second pump 502 which may be the same as pump 402. Valve $V_6$ is connected to atmosphere and to valve $V_4$ by line 406. Valve $V_5$ is connected to valves $V_3$, $V_{20}$, and $V_{21}$ by line 408. The vacuum side of pump 402 is connected to valves $V_3$ and $V_4$ by line 410.

Valve $V_{21}$ is connected to vacuum tank 372 by line 412. A line 414 leads from main tank 344 to valves $V_{22}$ and $V_{20}$. Valve $V_{22}$ is also connected to the pressure side of pump 502 by line 418. Finally, manifold 400 includes a drain line 420 controlled by valve $V_{10}$ which allows vacuum tank 372 to be drained of aspirated liquid.

Manifold 500 includes six valves which are used in the rinse side of the device and which allow pump 502 to be ganged to pump 402. Valves $V_{14}$ and $V_{16}$ are connected to atmosphere by line 504. Line 418 is connected to valves $V_{15}$, $V_{16}$, $V_{18}$, and $V_{19}$. The remainder of the rinsing side and manifold 500 connections will be described in detail later.

The cleaning cycle operation of the device is run as follows:

The clean cycle is selected and the catheter manufacturer and model number are selected. If the catheter has not been previously reused, a serial number is selected. Otherwise, the assigned serial number is reused. The chart entitled Cleaning Operation identifies valve and pump conditions during each step listed below.

PHASE I 0.1 RESTORING THE SYRINGE 364—The clean side stepper motor 366 is activated and pushes the plunger of the syringe 364 upward to expel any fluid or air from the syringe and leave the syringe in its fully up position.

0.2 PRESSURIZING MAIN TANK 344—The main fluid tank 344 is pressurized using air pump 402. This prepares the system for emptying the tank.

0.3 PURGING MAIN TANK 344—The main tank 344 is emptied to a preset level as indicated by load cell 424. All excess fluid from tank 344 is drained via the cassette. Load cell 424 may be HBM Model PLC available from Hottinger Baldwin Measurement, Inc. of Framingham, Mass.

0.4 PURGING VACUUM TANK 372—The vacuum tank 372 is pressurized using the air pump 402 and its contents drained directly out the system's drain port 420. This is a timed function (Approximately 20 seconds).

0.5 DE-PRESSURIZING MAIN TANK 344—Using the air pump 402, a vacuum is applied to the main tank 344 in preparation of filling it with cleaner fluid from line 348.

0.6 FILLING MAIN TANK 344 WITH FLUID—The cleaner fluid is admitted into the tank 344 and a load cell 424 monitors the tank weight. When approximately 200 ml of cleaner fluid is in the tank, this step is completed.

0.7 EVACUATING VACUUM TANK 372—Using both air pumps 402, 502 in series, a strong vacuum (approximately −700 mm Hg) is pulled on the vacuum tank 372. This tank 372 is used as a vacuum source to later aspirate (empty) the balloon.

0.8 SEAL OFF VACUUM TANK—Valves are closed to temporarily isolate vacuum tank 372 from the system.

0.9 PRESSURIZING MAIN TANK 344—The main tank 344 and its contents, the cleaner fluid, is put under pressure of approximately 10 PSI (600 mm Hg). The main tank 344 then acts as a source for fluid to infuse (fill) the balloon 20.

0.10 SEAL OFF MAIN TANK—The main tank 344 is sealed off from the system by closing valves.

0.11 ASPIRATE THE BALLOON—The vacuum of the vacuum tank is applied to the catheter's balloon. This vacuum then draws out air & "dirty" fluid from the balloon. The vacuum is applied for approx. 2 minutes.

PHASE II

During this phase of the cleaning process, the balloon is alternatively aspirated and infused (emptied and filled) with cleaner fluid.

0.16 SEAL OFF VACUUM TANK—The vacuum tank is sealed in preparation of pressurizing the main tank.

0.17 PRESSURIZING THE MAIN TANK—The main tank is pressurized to approximately 10 PSI and sealed.

0.18 SEAL OFF MAIN TANK—Main tank 344 is sealed off from the system.

1.1 and 1.2 ASPIRATE BALLOON—The vacuum of the vacuum tank is applied to the catheter's balloon for approximately 5 seconds. The two air pumps are in series and constantly draw on the vacuum tank to maintain its vacuum. The aspirated balloon 20 is then sealed from the vacuum source by closing valve $V_{11}$.

1.3 and 1.4 FILLING BALLOON—The cleaner fluid (sterilant) in the main tank is applied to the catheter's balloon for about 4 seconds. The fluid fills the balloon to approximately 50% of the balloon's volume. The balloon is sealed off from tank 344 by closing valve $V_9$.

(The above two steps aspiration & filling are repeated 24 times).

PHASE III

During this phase, the balloon will be tested at maximum operating pressure (eg. 90 PSI) and the lumen (inner, open-ended tube of the catheter) and outer body of the catheter will be cleaned.

25.1 VENT MAIN TANK/ASPIRATE BALLOON—Pressure is relieved from the tank 344 and the balloon 20 is aspirated using the vacuum tank 372 to remove all cleaner fluid and air in preparation of the balloon pressure test.

25.2 FILL SYRINGE 364—The clean side stepper motor 366 is activated to pull down the syringe's plunger and draw cleaner fluid from the main tank 344. Approximately 4 ml of fluid is in the syringe.

25.3 PURGE SYRINGE—The plunger of the syringe 364 is moved up 1 ml to purge the syringe of any air.

25.4 VENT SYRINGE—Residual pressure in the syringe 364 is allowed to escape (into main tank).

25.5 SEAL MAIN TANK—Valves are closed to isolate the main tank 344 from the system.

25.6 TEST VOL./PRESS. OF BALLOON—The stepper motor 366 is used to single-step the plunger (1 step is approximately 2 microliters) of syringe 364 thus applying a steadily increasing pressure to the balloon. A pressure transducer 380 monitors this pressure. When the set-point pressure is reached, the pressure test is complete. Simultaneously, the steps are recorded with their corresponding pressure. This creates a pressure/volume curve or table from which the volume of the balloon is determined. Also during this step, the machine will determine if the balloon leaks, is blocked, or has a volume out of range of the manufacturer's specifications. At the completion of the pressure test, the syringe plunger is pulled down, depressurizing the balloon but leaving it filled with cleaner fluid.

25.7 PURGING SYRINGE—The remaining cleaner fluid is purged from the syringe 364, leaving the syringe ready for the next user.

25.8 PRESSURIZING MAIN TANK—Pressure is applied to the main tank 344 from both pumps 402, 502.

25.9 CLEANING LUMEN—About 30 ml of cleaner fluid is flushed through the lumen 14 of the catheter 10. The machine monitors this flow via the load cell 424 and checks for blockage of the lumen. Blockage would be indicated if no decrease in the weight of main tank 344 is measured by the load cell.

25.10 CLEANING CASSETTE 100—Approximately 150 ml of cleaner fluid is flushed through the cassette, cleaning the outside of the catheter 10 and leaving the cassette filled with cleaner fluid.

25.11 DE-PRESSURIZING CASSETTE—Residual pressure in the cassette 10 is allowed to bleed off.

25.12—CLEANING COMPLETED—At this time, cleaning is completed and all valves are normally closed except for valves $V_{18}$, $V_{19}$ which are normally open.

25.13—VENTING LINES—A vacuum is pulled on the lumen 134, cassette inlet 156 and cassette drain lines 150 prior to the removal of the cassette from the machine so that the user will not get cleaner fluid on his/her hands.

PHASE IV

During Phase IV, the cassette is capped and pressurized. Also, data is stored on disk and printed out for the user.

25.14 REMOVE CASSETTE FROM MACHINE—At this time, the cassette 10 is detached from its connector 300 and a special cap 270 is affixed to the cassette's port. The entire assembly, cassette plus cap, is then re-connected to the port interface manifold 300.

25.15 PRESSURIZING THE CASSETTE—The main tank 344 is pressurized and cleaner is injected into the cassette 10. The cap 270 has a one-way valve 278 which allows cleaner fluid to enter but not leave the cassette. After approx. 20 seconds, the cassette is pressurized to about 4 PSI.

25.16 VENT LINES—A vacuum is then applied to the connector lines so that the user will not get drops of cleaner fluid on his/her hands when disconnecting the cassette 10 from manifold 300.

25.17 PRESSURIZATION COMPLETED—The machine stores data to disk (pressure/volume characteristics, time and date, number of reuses, etc.), and prints out a label to the user. A copy of the label is displayed on the screen in case of printer malfunction.

The pressurized cassette 100 with cleaner within and surrounding catheter 10 is stored for between at least eleven hours and two weeks before being rinsed and reused. Pressure indicator 250 is designed such that end 266 of plunger 262 projects above body 260 when under pressure. Coloring end 266 with a distinctive color makes it very easy to tell if the cassette has remained sealed during this long disinfecting period. If the pressure indicator shows that the seal is maintained at the end of the disinfecting period, the cassette is ready to be rinsed of the cleaner fluid.

The cleaner fluid functions to clean and sterilize catheter 10. Preferably, the cleaner fluid contains per-acids such as peracetic acid, whose strong oxidizing action provides good cleaning and disinfecting properties. As shown in the drawings, manifold 340 is connected to a water source by line 342. In this manner, concentrated cleaner fluid may be diluted within main tank 344 by admitting water past valve $V_1$.

RINSE SIDE

The rinse side of the catheter reprocessor is utilized to remove all traces of cleaner fluid from the catheter while maintaining sterility. All of the following steps require the use of aseptic technique to ensure that sterility of the catheter is maintained. A sterile tubing set 600 is used to connect the cassette 100 to the rinse side. Tubing set 600 includes a port interface manifold 602 which is identical to manifold 300. Line 604 leads from a port of manifold 602 to a drain fitting 606 and to a syringe needle 608. Drain fitting 606 is secured to cassette pressure relief manifold 610 which in turn is connected to a drain by line 612. Line 612 includes a check valve 614 to prevent flow from the drain to manifold 610.

Line 616 leads from the balloon port 618 of port interface manifold 602 to a 3-way stopcock 620 controlled by drive motor 622. 3-way stopcock 620 is connected to a syringe pump 630 which is driven by a stepper motor 632 which may be identical to stepper motor 366. A limit switch 634 is contacted to shut down the stepper motor 632 when the plunger of the syringe pump 630 is fully depressed. No portion of limit switch 634 is in contact with the sterile interior of syringe pump 630. Line 616 enters the bottom of a drip bulb 640.

Line 642 leads from lumen port 644 of port interface manifold 602 and enters the bottom of drip bulb 640. Line 646 leads from the cassette drain port 648 of manifold 602 and enters the bottom of drip bulb 640. The upper end of drip bulb 640 is connected to line 652 which is connected to a bag of normal saline 654 via spike 656. Line 652 includes a check valve 658 to prevent flow from drip bulb 640 to saline bag 654. A manually controllable clamp valve 660 further controls flow in line 652.

Drip bulb 640 is connected to a foam detector 664 such as the type described in U.S. Pat. No. 4,068,521 to Louis C. Cosentino et al which issued Jan. 17, 1978. Foam detector 664 transmits ultrasonic energy through drip bulb 640 and the received signal is sensed by a receiving lens. The signal from the foam detector varies when full versus empty. The signal is used to indicate the fill level of the drip bulb.

Manifold 500 is used in both the rinse mode and cleaning mode of reprocessing. Line 418 is connected between the pressure output of air pump 502 and valves $V_{15}$, $V_{16}$, $V_{18}$, and $V_{19}$. Valves $V_{18}$ and $V_{19}$ are three way valves which may be bled to atmosphere or connected to lines 506 and 508 respectively. The air pressure within lines 506 and 508 is used to activate pneumatic valves PVA-2 and PVA-1. Valve PVA-1 is a pinch valve which when pressurized pinches line 646 shut. Likewise, Valve PVA-2 is a pinch valve which pinches line 642 shut when pressurized. In this manner, no portion of valve PVA-1 or PVA-2 contacts the interior of lines 646 or 642. Thus, PVA-1 and PVA-2 do not need to be sterile. Line 512 leads from valves $V_{13}$ and $V_{15}$ to enter the top of drop bulb 640. A transducer protector 514 consisting of a 0.5 micron filter is used to filter airflow through line 514 from valve $V_{15}$ to prevent microbes from being introduced into the sterile tube set 600 through drip bulb 640. Additionally, transducer protectors 516 and 518 are connected in line 404 as shown and transducer protector 411 filters line 410.

RINSE PROCEDURE

The rinse cycle is selected as are the catheter manufacturer, model number and serial number.

A sterile tube set 600 is connected as shown in FIGS. 11a, 11b, 12a and 12b. Manual clamp 660 is shut and spike 656 is inserted into a 500 ml bag 654 of sterile saline.

A properly cleaned and disinfected catheter 10 within a pressurized cassette 100 is depressurized by inserting syringe needle 608 into valve fitting 274 which opens duck bill valve 278 and depressurizes the case. Plug 270 is removed and port interface manifold 602 is connected to the cassette ports, 134, 140, 156 and 150. Port 151 is a blank.

The catheter is then processed as follows; the chart entitled Rinsing Operation identifies the valve and pump conditions during each step listed below:

During Phase I the cassette is purged off the sterilant (cleaner fluid) and filled with sterile air.

PHASE I

Purging Cassette—The two air pumps 402, 502 are run in series to provide approximately 10 psi with which to purge the cassette of its sterilant. This is a timed function (approximately 15 seconds).

Evacuating the Balloon—This a complex step in which several functions occur simultaneously:

The stopcock motor 622 is activated and rotates the stopcock 620 ninety degrees clockwise to open a fluid path between the rinse-side syringe pump 630 and the catheter's balloon 20; the syringe pump is activated via the stepper motor 632 and is pulled down to draw a vacuum on the balloon; the vacuum is held for approximately one minute to enable almost all of the sterilant in the balloon to migrate into the syringe; during this time, the drip bulb 640 is alternatively filled and purged, pushing sterile rinse fluid (saline) through the cassette (an ultrasonic level detector 664 monitors the amount of saline in the drip bulb). Each time the drip bulb is indicated as full, the purge drip bulb cycle is started until a preselected number of cycles have run.

Filling Drip Bulb—The drip bulb is filled in preparation of rinsing the lumen. Vacuum is still applied to the balloon.

Rinsing Lumen—The pinch valve on the lumen line is opened and allows the saline in the drip bulb to be pushed through the lumen using both air pumps in series. This is a timed function and if the Detector 664 detects that fluid still remains in the drip bulb after this time (40 sec) then the computer concludes that the lumen is blocked and fails the catheter.

PHASE II

During Phase II the balloon is rinsed using the syringe 630. Also, the pumps 502, 402 and drip bulb 640 rinse the cassette and catheter body. This process is repeated for fifteen cycles.

Turning Stopcock Counter Clockwise—The stopcock motor 622 is activated and turns the stopcock 620 so that a fluid path is open between the syringe 630 and drip bulb 640.

Purging Drip Bulb/Syringe—The syringe is pushed up and fluid is expelled into the drip bulb 640. At the same time the air pumps 502, 402 are activated and the pinch valves PVA-1, PVA-2 opened so that the contents of the drip bulb are purged out through the cassette.

Filling Drip Bulb—A vacuum is drawn on the drip bulb using the air pumps, the pinch valves are closed and the drip bulb fills to a predetermined level detected by the ultrasonic level detector 664.

Filling Syringe—The syringe is drawn down and fills with fluid from the drip bulb (approximately 2 ml).

Turning Stopcock Clockwise—A fluid path is opened from the syringe to the balloon.

Filling Balloon—The syringe is pushed up and fluid is forced into the balloon at approximately 20 psi.

Evacuating the Balloon—The syringe is drawn down, pulling a vacuum on the balloon, and held for approximately 30 seconds. Also, during this time, the drip bulb is alternately filled and purged, pushing saline and air through the cassette.

PHASE III

During this phase, the balloon is tested for pressure.

Turning Stopcock Counter Clockwise—Opens fluid path between syringe and drip bulb.

Purging Drip Bulb/Syringe—The syringe is pushed up and fluid is expelled into the drip bulb 640. At the same time the air pumps 502, 402 are activated and the pinch valves PVA-1, PVA-2 opened so that the contents of the drip bulb are purged out through the cassette.

Filling Drip Bulb—A vacuum is drawn on the drip bulb using the air pumps, the pinch valves are closed and the drip bulb fills to a predetermined level detected by the ultrasonic level detector 664.

Filling Syringe—The syringe is drawn down and fills with fluid from the drip bulb (approximately 2 ml).

Turning Stopcock Clockwise—Opens fluid path to balloon.

Testing Balloon—The syringe is pushed up at a rate which will cause the stepper motor to stall when the test pressure of the balloon is reached. If the stepper motor does not stall (i.e. there is a leak in the balloon) the syringe will actuate a micro-switch (limit switch 634) to indicate a fault with the balloon.

Evacuating the Balloon—The syringe is drawn down and a vacuum is pulled on the balloon.

Turning Stopcock Counter Clockwise—Opens fluid path between syringe and drip bulb.

Purging Cassette—Syringe is pushed up and drip bulb is purged.

Filling Drip Bulb—A vacuum is drawn on the drip bulb using the air pumps, the pinch valves are closed and the drip bulb fills to a predetermined level detected by the ultrasonic level detector 664.

Purging Drip Bulb—The syringe is pushed up and fluid is expelled into the drip bulb 640. At the same time the air pumps 502, 402 are activated and the pinch valves PVA-1, PVA-2 opened so that the contents of the drip bulb are purged out through the cassette.

Purging Cassette—The cassette is purged of fluid using air from the air pumps through the drip bulb.

Purging Lumen—The lumen is purged of fluid using air form the air pumps through the drip bulb.

Rinsing Completed—The rinsing process is completed and the machine awaits the user's removal of the cassette and tubing set.

When the rinsing is completed the tubing set is disconnected from cassette 100. A sterile cap 270 is fitted into the ports of the cassette. The roller clamp 660 is closed on saline line 652. To use the reprocessed catheter, the cassette is opened by loosening knob 212 and separating the cassette into upper 120 and lower 180 halves. Using sterile techniques, the balloon lines and infusion lines are pulled free of the pinch points without allowing catheter or hands to touch the outside of the cassette. Connectors 22 and 24 are disconnected and the tray 110 and catheter 10 are removed from the cassette and transferred to a sterile field to await reuse.

In considering the invention, it must be remembered that the disclosure is illustrative only and that the scope of the invention is to be determined by the appended claims. For example, catheters having additional lumens or balloons may be reprocessed by a catheter reprocessing system in accordance with the invention by merely adding elements similar to those described for reprocessing single lumens and or balloons.

What is claimed is:

1. A system for reprocessing catheters having a catheter hub, body, at least two lumens and a balloon; said system comprising:
   (a) cleaning means for supplying catheter cleaning solution to the lumens and outside of a catheter;
   (b) balloon test means for testing the balloon strength and filling volume and for displaying strength and volume date;
   (c) rinsing means for removing said cleaning solution from the catheter; and
   (d) means for monitoring the condition of the catheter during reprocessing.

2. The system of claim 1 wherein said monitoring means measures indicia of usability of said catheter.

3. The system of claim 2 further including means responsive to said monitoring means for selectively controlling the sequencing of the reprocessing procedures in response to the condition of said catheter to prohibit the use of defective catheters.

4. The system of claim 3 further comprising means for storing predetermined criteria which a catheter must meet in order to be usable.

5. The system of claim 4 wherein said controlling means compares indicia of usability of said catheter to balloon strength and volume data and inhibits further reprocessing if said data does not meet said predetermined criteria.

6. The system of claim 1 wherein said balloon test means measures the volume of said balloon at preselected, varied pressures.

7. The system of claim 1 further including storage means for storing a catheter surrounded with cleaning solution, said means including a catheter case into which a catheter is insertable, said case including a plurality of ports constructed and arranged such that access to the exterior and interior of the catheter is possible form the outside of the case, each of said ports being normally closed until engaged with said cleaning means, balloon test means or rinsing means.

8. The system of claim 7 wherein said case further includes means for indicating whether said case is sealed under pressure.

9. A cleaner for reprocessing catheters of the type having a catheter hub, body, lumens and a balloon, said cleaner comprising:
   (a) cleaning means for supplying catheter cleaning solution to the lumens and outside of a catheter;
   (b) balloon test means for testing the balloon strength and filling volume and for displaying strength and volume data;
   (c) storage means for storing a catheter surrounded with cleaning solution;
   (d) rinsing means for removing all traces of cleaning solution from the catheter;
   (e) a computer including a memory, said computer having means for generating commands in accordance with programmed instructions for directing said cleaning means, balloon test means and rinse means for directing catheter reprocessing and for displaying data; and
   (f) a control console coupled to said computer for inserting programmed instructions therein.

10. A system for reprocessing catheters having a catheter hub, body at least two lumens and a balloon, said system comprising:
    (a) cleaning means for supplying catheter cleaning solution through the lumens and around the exterior of a catheter;
    (b) balloon test means for testing the balloon volume at preselected pressures and comparing such volume and pressure data to the specification for unused catheters;
    (c) rinsing means for removing said cleaning solution from the catheter and maintaining the sterility of the cleaned catheter during rinsing, said rinsing means further including means for testing the integrity of said balloon by applying fluid under pressure to said balloon until either a preselected pressure is reached or a limit switch is contacted to stop fluid flow; and
    (d) means for monitoring the condition of the catheter during reprocessing.

11. The system of claim 10 wherein said monitoring means measures indicia of usability of said catheter.

12. The system of claim 11 further including means responsive to said monitoring means for selectively controlling the sequencing of the reprocessing procedures in response to the condition of said catheter to prohibit the use of defective catheters.

13. The system of claim 12 further comprising means for storing predetermined criteria which a catheter must meet in order to be usable.

14. The system of claim 13 wherein said controlling means compares indicia of usability of said catheter to balloon strength and volume data and inhibits further reprocessing if said data does not meet said predetermined criteria.

15. The system of claim 14 further including storage means for storing a catheter surrounded with cleaning solution, said means including a catheter case into which a catheter is insertable, said case including a plurality of ports, said ports being constructed and arranged such that access to the exterior and interior of the catheter is possible from the outside of the case, each of said ports being normally closed until engaged with said cleaning means, balloon test means or rinsing means.

16. The system of claim 15 wherein said case further includes means for indicating whether said case is sealed under pressure.

* * * * *

UNITED STATES PATENT AND TRADEMARK OFFICE
CERTIFICATE OF CORRECTION

PATENT NO. : 4,721,123

DATED : January 26, 1988

INVENTOR(S) : COSENTINO, ET AL

It is certified that error appears in the above-identified patent and that said Letters Patent is hereby corrected as shown below:

Insert the nine attached chart pages referred to at Col. 5, after line 58 at the end of the specification.

Signed and Sealed this

Eighteenth Day of August, 1992

Attest:

DOUGLAS B. COMER

*Attesting Officer*  *Acting Commissioner of Patents and Trademarks*

CATHETRON RINSING OPERATION

| Valve or Motor / Process Step | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | $V_{13}$ |
|---|---|---|---|---|---|---|---|---|---|---|---|---|---|
| Purging Cassette | - | - | - | 0 | - | - | - | - | - | - | - | - | - |
| Evacuating Balloon* | \multicolumn{10}{c}{SEE NOTE AT BOTTOM OF PAGE} | | | | | | | | | | | cw | off | dwn |
| Filling drip bulb | - | - | - | - | - | - | - | - | - | - | - | - | 0 |
| Rinsing Lumen | - | - | - | 0 | - | - | - | - | - | - | - | - | - |
| | | | | | | | | | | | | | |
| Turning Stopcock Cntr. Clockwise | - | - | - | - | - | - | - | - | - | - | - | - | - |
| Purging drip bulb/syringe | - | - | - | 0 | - | - | - | - | - | - | - | - | - |
| Filling drip bulb | - | - | - | - | - | - | - | - | - | - | - | - | 0 |
| Filling syringe | - | - | - | - | - | - | - | - | - | - | - | - | - |
| Turning stopcock clockwise | - | - | - | - | - | - | - | - | - | - | - | - | - |
| Filling balloon | - | - | - | - | - | - | - | - | - | - | off | off | dwn |
| Evacuating balloon* | SEE NOTE AT BOTTOM OF PAGE | | | | | | | | | | off | off | dwn |
| | | | | | | | | | | | | | |
| Turning stopcock contr. clockwise | - | - | - | - | - | - | - | - | - | - | - | - | - |
| Purging drip bulb/syringe | - | - | - | 0 | - | - | - | - | - | - | - | - | - |
| Filling drip bulb | - | - | - | - | - | - | - | - | - | - | - | - | 0 |
| Filling syringe | - | - | - | - | - | - | - | - | - | - | - | - | - |
| Turning stopcock clockwise | - | - | - | - | - | - | - | - | - | - | - | - | - |
| Testing balloon | - | - | - | - | - | - | - | - | - | - | - | - | - |
| Evacuating Balloon* | SEE NOTE AT BOTTOM OF PAGE | | | | | | | | | | off | off | dwn |
| Turning stopcock contr. clockwise | - | - | - | - | - | - | - | - | - | - | - | - | - |
| Purging cassette | - | - | - | 0 | - | - | - | - | - | - | - | - | - |
| Filling drip bulb | - | - | - | - | - | - | - | - | - | - | - | - | 0 |

Pg 1 of 9

| CATHETRON RINSING OPERATION (CONT) | | | | | | | | | | | Pg | 2 | of 9 |
|---|---|---|---|---|---|---|---|---|---|---|---|---|---|
| Valve or Motor / Process Step | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | $V_{13}$ |
| Purging drip bulb | - | - | - | O | - | - | - | - | - | - | - | - | - |
| Purging cassette | - | - | - | O | - | - | - | - | - | - | - | - | - |
| Purging Lumen | - | - | - | O | - | - | - | - | - | - | - | - | - |
| ** Fill Drip Bulb | - | - | - | - | - | - | - | - | - | - | - | - | - |
| ** Purge Drip Bulb | - | - | - | O | - | - | - | - | - | - | - | - | - |

SYMBOLS: Circle (O) = valve open    CW = clockwise
Dash (-) = valve closed    CCW = counter clockwise

*NOTE: During the evacuation of the balloon, the machine concurrently flushes out the cassette with saline. It does this by alternating the two steps, filling drip bulb and purging drip bulb, while holding the syinge in the down position.

| Valve or Motor / Process Step | $V_{14}$ | $V_{15}$ | $V_{16}$ | $V_{18}$ | $V_{19}$ | $V_{20}$ | $V_{21}$ | $V_{22}$ | 402 CLN AIR PMP | 502 RNS AIR PMP | 622 STOP COCK MTR | 364 CLN SYR PMP | 630 RNS SYR PMP |
|---|---|---|---|---|---|---|---|---|---|---|---|---|---|
| Purging Cassette | - | O | - | O | O | - | - | - | on | on | off | off | off |
| Evacuating Balloon * | | | | SEE NOTE AT BOTTOM OF PAGE | | | | | | | cw | off | dwn |
| Filling drip bulb | - | - | O | - | - | - | - | - | off | on | off | off | off |
| Rinsing Lumen | - | O | - | O | - | - | - | - | on | on | off | off | off |
| | | | | | | | | | | | | | |
| Turning Stopcock Cntr. Clockwise | - | - | - | - | - | - | - | - | off | off | CCW | off | off |
| Purging drip bulb/syringe | - | O | - | O | O | - | - | - | on | on | off | off | up |
| Filling drip bulb | - | - | O | - | - | - | - | - | off | on | off | off | off |

Patent No. 4,721,123

| Cathetron Rinsing Operation Cont. | | | | | | | | | | | | | Page 3 of 9 | |
|---|---|---|---|---|---|---|---|---|---|---|---|---|---|
| Valve or Motor<br>Process Step | $V_{14}$ | $V_{15}$ | $V_{16}$ | $V_{18}$ | $V_{19}$ | $V_{20}$ | $V_{21}$ | $V_{22}$ | 402 CLN AIR PMP | 502 RNS AIR PMP | 622 STOP COCK MTR | 364 CLN SYR PMP | 630 RNS SYR PMP |
| Filling syringe | - | - | - | - | - | - | - | - | off | off | off | off | dwn |
| Turning stopcock clockwise | - | - | - | - | - | - | - | - | off | off | CW | off | off |
| Filling balloon | 0 | 0 | - | 0 | 0 | - | - | - | off | on | off | off | up |
| Evacuating balloon* | SEE NOTE AT BOTTOM OF PAGE | | | | | | | | | | off | off | dwn |
| | | | | | | | | | | | | | |
| Turning stopcock contr. clockwise | - | - | - | - | - | - | - | - | off | off | CCW | off | off |
| Purging drip bulb/syringe | - | 0 | - | 0 | 0 | - | - | - | on | on | off | off | up |
| Filling drip bulb | - | - | 0 | - | - | - | - | - | off | on | off | off | off |
| Filling syringe | - | - | - | - | - | - | - | - | off | off | off | off | dwn |
| Turning stopcock clockwise | - | - | - | - | - | - | - | - | off | off | CW | off | off |
| Testing balloon | - | - | - | - | - | - | - | - | off | off | off | off | up |
| Evacuating Balloon* | SEE NOTE AT BOTTOM OF PAGE | | | | | | | | | | off | off | dwn |
| Turning stopcock cntr. clockwise | - | - | - | - | - | - | - | - | off | off | CCW | off | off |
| Purging cassette | - | 0 | - | 0 | 0 | - | - | - | on | on | off | off | up |
| Filling drip bulb | - | - | 0 | - | - | - | - | - | off | on | off | off | off |
| Purging drip bulb | - | 0 | - | 0 | 0 | - | - | - | on | on | off | off | off |
| Purging cassette | - | 0 | - | 0 | 0 | - | - | - | on | on | off | off | off |
| Purging lumen | - | 0 | - | 0 | - | - | - | - | on | on | off | off | off |
| ** Fill drip bulb | - | 0 | - | - | - | - | - | - | off | on | CWf | off | dwn |
| **Purge Drip Bulb | - | 0 | - | 0 | 0 | - | - | - | on | on | CW | off | dwn |

SYMBOLS Circle (0) = valve open   CW = clockwise   Dash (-) = valve closed   CCW = counter clockwise
*NOTE: During the evacuation of the balloon, the machine concurrently flushes out the cassette with saline. It does this by alternating the two steps, filling drip bulb and purging drip bulb, while holding the syringe in the down position.

CATHETRON CLEANING OPERATION

Symbols : circle (0) = valve open
dash (-) = valve closed

| Valve Or Motor / Process Step | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | $V_{13}$ |
|---|---|---|---|---|---|---|---|---|---|---|---|---|---|
| 0.1 Restoring The Syringe | - | - | - | - | - | - | 0 | 0 | 0 | - | - | 0 | - |
| 0.2 Pressurizing Main Tank | - | - | - | 0 | 0 | - | - | - | - | - | - | - | - |
| 0.3 Purging Main Tank | - | - | - | 0 | - | - | 0 | 0 | - | - | - | 0 | - |
| 0.4 Purging Vacuum Tank | - | - | - | 0 | 0 | - | - | - | - | 0 | - | - | - |
| 0.5 Depressurizing Main Tank | - | - | 0 | - | - | - | - | - | - | - | - | - | - |
| 0.6 Filling main tank w/ fluid | 0 | - | 0 | - | - | - | - | - | - | - | - | - | - |
| 0.7 Evacuating Vac. Tank | - | - | 0 | - | - | - | - | - | - | - | 0 | - | - |
| 0.8 Seal Off Vacuum Tank | - | - | 0 | - | - | - | - | - | - | - | 0 | - | - |
| 0.9 Pressurizing Main Tank | - | - | - | 0 | - | - | - | - | - | - | - | 0 | - |
| 0.10 Seal Off Main Tank | - | - | 0 | - | - | - | - | - | - | - | - | - | - |
| 0.11 Filling Syringe (≃1ml) | - | - | 0 | 0 | - | - | - | - | 0 | - | - | - | - |
| 0.12 Purge Syringe | - | - | 0 | 0 | - | - | - | - | - | - | 0 | - | - |
| 0.13 Seal Off Main Tank | - | - | 0 | - | - | - | - | - | - | - | - | - | - |
| 0.14 Aspirating Balloon | - | - | 0 | - | - | - | - | - | - | - | 0 | 0 | - |
| 0.15 Aspirating Balloon (seal off) | - | - | 0 | - | - | - | - | - | - | - | 0 | 0 | - |

| Cathetron Cleaning Operation Cont. | | | | | | | | | | | Pg | 5 | of | 9 |
|---|---|---|---|---|---|---|---|---|---|---|---|---|---|---|
| Valve or Motor Process Step | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | $V_{13}$ |
| 0.16 Seal Off Vac. Tank | - | - | 0 | - | - | - | - | - | - | - | 0 | - | - |
| 0.17 Pressurizing Main Tank | - | - | - | 0 | - | - | - | - | - | - | - | 0 | - |
| 0.18 Seal Off Main Tank | - | - | 0 | - | - | - | - | - | - | - | - | - | - |
| | | | | | | | | | | | | | |
| 1.1 Aspirate Balloon | - | - | 0 | - | - | - | - | - | - | - | 0 | - | - |
| 1.2 Aspirate Balloon (seal) | - | - | 0 | - | - | - | - | - | - | - | - | - | - |
| 1.3 Filling Balloon | - | - | 0 | - | - | - | - | - | 0 | - | - | - | - |
| 1.4 Filling Balloon (seal) | - | - | 0 | - | - | - | - | - | - | - | - | - | - |
| | | | | | | | | | | | | | |
| 25.1 Vent Main Tank/Aspirate Balloon | - | - | 0 | 0 | 0 | 0 | - | - | - | - | 0 | 0 | - |
| 25.2 Fill Syringe | - | - | 0 | 0 | 0 | 0 | - | - | 0 | - | - | - | - |
| 25.3 Purge (1 ml) syringe | - | - | 0 | 0 | 0 | 0 | - | - | - | - | 0 | - | - |
| 25.4 Vent Syringe | - | - | 0 | 0 | 0 | 0 | - | - | 0 | - | - | - | - |
| 25.5 Seal Main Tank | - | - | - | - | - | - | - | - | - | - | - | - | - |
| 25.6 Test Vol./Press. of Balloon | - | - | - | - | - | - | - | - | - | - | - | 0 | - |
| (25.6A De-Press. Balloon) | - | - | - | - | - | - | - | - | - | - | - | 0 | - |
| 25.7 Purging Syringe | - | - | 0 | 0 | - | - | - | - | - | - | 0 | - | - |
| 25.8 Pressurizing main tank | - | - | - | 0 | - | - | - | - | - | - | - | - | - |

| Cathetron Cleaning Operation Cont. | | | | | | | | | | | Pg | 6 | of | 9 |
|---|---|---|---|---|---|---|---|---|---|---|---|---|---|---|
| Valve or Motor / Process Step | $V_1$ | $V_2$ | $V_3$ | $V_4$ | $V_5$ | $V_6$ | $V_7$ | $V_8$ | $V_9$ | $V_{10}$ | $V_{11}$ | $V_{12}$ | $V_{13}$ |
| 25.9 Cleaning Lumen | - | - | - | O | - | - | O | - | - | - | - | O | - |
| 25.10 Cleaning Cassette | - | - | - | O | - | - | - | O | - | - | - | O | - |
| 25.11 De-pressurizing cassette | - | - | O | - | - | - | - | - | - | - | - | O | - |
| 25.12 Cleaning completed | - | - | - | - | - | - | - | - | - | - | - | - | - |
| 25.13 Venting lines | - | - | O | - | - | - | - | O | - | - | - | - | - |
| 25.14 Disconnect cassette, attach cap and re-connect | - | - | O | - | - | - | - | O | - | - | - | - | - |
| 25.15 Pressurizing the cassette | - | - | - | O | - | - | - | O | - | - | - | - | - |
| 25.16 Vent lines | - | - | O | - | - | - | - | O | - | - | - | - | - |
| 25.17 Pressurization completed | - | - | - | - | - | - | - | - | - | - | - | - | - |

CATHETRON CLEANING OPERATION

Symbols : circle (0) = valve open
dash (-) = valve closed

| Valve Or Motor / Process Step | $V_{14}$ | $V_{15}$ | $V_{16}$ | $V_{18}$ | $V_{19}$ | $V_{20}$ | $V_{21}$ | $V_{22}$ | CLN AIR PMP | RNS AIR PMP | STOP COCK MTR | CLN SYR PMP | CLN SYR PMP |
|---|---|---|---|---|---|---|---|---|---|---|---|---|---|
| 0.1 Restoring The Syringe | - | - | - | O | O | - | - | - | off | off | off | up | off |
| 0.2 Pressurizing Main Tank | - | - | - | O | O | O | - | - | on | off | off | off | off |
| 0.3 Purging Main Tank | - | - | - | O | O | - | - | O | on | on | off | off | off |

Patent No. 4,721,123

| Cathetron Cleaning Operation Cont. | | | | | | | | | | | | | | Pg 7 of 9 |
|---|---|---|---|---|---|---|---|---|---|---|---|---|---|---|
| Valve or Motor / Process | $V_{14}$ | $V_{15}$ | $V_{16}$ | $V_{18}$ | $V_{19}$ | $V_{20}$ | $V_{21}$ | $V_{22}$ | CLN AIR PMP | RNS AIR PMP | STOP COCK MTR | CLN SYR PMP | CLN SYR PMP |
| 0.4 Purging Vacuum Tank | - | - | - | O | O | - | O | - | on | off | off | off | off |
| 0.5 Depressurizing Main Tank | - | - | O | O | O | O | - | - | on | on | off | off | off |
| 0.6 Evacuating Vac Tank | - | - | O | O | O | O | - | - | on | on | off | off | off |
| 0.7 Evacuating Vac. Tank | - | - | O | O | O | - | O | - | on | on | off | off | off |
| 0.8 Seal Off Vacuum Tank | - | - | O | O | O | - | - | - | on | on | off | off | off |
| 0.9 Pressurizing Main Tank | - | - | - | O | O | - | - | O | on | on | off | off | off |
| 0.10 Seal Off Main Tank | - | - | - | O | O | - | - | - | on | on | off | off | off |
| 0.11 Filling Syringe (1 ml) | - | - | - | O | O | - | - | - | off | off | off | dwn | off |
| 0.12 Purge Syringe | - | - | - | O | O | - | - | - | off | off | off | up | off |
| 0.13 Seal Off Main Tank | - | - | - | O | O | - | - | - | on | on | off | off | off |
| 0.14 Aspirating Balloon | - | - | O | O | O | - | O | - | on | on | off | off | off |
| 0.15 Aspirating Balloon (seal off) | - | - | O | O | O | - | - | - | on | on | off | off | off |
| 0.16 Seal Off Vac. Tank | - | - | - | O | O | - | - | - | on | on | off | off | off |
| 0.17 Pressurizing Main Tank | - | - | - | O | O | - | - | O | on | on | off | off | off |
| 0.18 Seal Off Main Tank | - | - | - | O | O | - | - | - | on | on | off | off | off |
| | | | | | | | | | | | | | |
| 1.1 Aspirate Balloon | - | - | O | O | O | - | O | - | on | on | off | off | off |

| Cathetron Cleaning Operation Cont. | | | | | | | | | | | | | |
|---|---|---|---|---|---|---|---|---|---|---|---|---|---|
| Valve or Motor / Process Step | $V_{14}$ | $V_{15}$ | $V_{16}$ | $V_{18}$ | $V_{19}$ | $V_{20}$ | $V_{21}$ | $V_{22}$ | CLN AIR PMP | RNS AIR PMP | STOP COCK MTR | CLN SYR PMP | RNS SYR PMP |
| 1.2 Aspirate Balloon (seal) | - | - | 0 | 0 | 0 | - | 0 | - | on | on | off | off | off |
| 1.3 Filling Balloon | - | - | 0 | 0 | 0 | - | 0 | - | on | on | off | off | off |
| 1.4 Filling Balloon (seal) | - | - | 0 | 0 | 0 | - | 0 | - | on | on | off | off | off |
| | | | | | | | | | | | | | |
| 25.1 Vent Main Tank/ Aspirate Balloon | - | - | - | 0 | 0 | 0 | - | - | off | off | off | off | off |
| 25.2 Fill Syringe | - | - | - | 0 | 0 | - | - | - | off | off | off | DWN | off |
| 25.3 Purge (1 ml) syringe | - | - | - | 0 | 0 | - | - | - | off | off | off | up | off |
| 25.4 Vent Syringe | - | - | - | 0 | 0 | - | - | - | off | off | off | off | off |
| 25.5 Seal Main Tank | - | - | - | 0 | 0 | - | - | - | off | off | off | off | off |
| 25.6 Test Vol./ Press. of Balloon | - | - | - | 0 | 0 | - | - | - | off | off | off | up | off |
| 25.6A Depress. Balloon | - | - | - | 0 | 0 | - | - | - | off | off | off | DWN | off |
| 25.7 Purging Syringe | - | - | - | 0 | 0 | - | - | - | off | off | off | up | off |
| 25.8 Pressurizing main tank | - | - | - | 0 | 0 | - | - | 0 | on | on | off | off | off |
| 25.9 Cleaning Lumen | - | - | - | 0 | 0 | - | - | 0 | on | on | off | off | off |
| 25.10 Cleaning Cass. | - | - | - | 0 | 0 | - | - | 0 | on | on | off | off | off |
| 25.11 Depressurizing cassette | - | 0 | - | 0 | 0 | 0 | - | - | off | on | off | off | off |
| 25.12 Cleaning completed | - | - | - | 0 | 0 | - | - | - | off | off | off | off | off |

| Cathetron Cleaning Operation Cont. | | | | | | | | | Pg | 9 | of | 9 | |
|---|---|---|---|---|---|---|---|---|---|---|---|---|---|
| Valve Or Motor / Process Step | $V_{14}$ | $V_{15}$ | $V_{16}$ | $V_{18}$ | $V_{19}$ | $V_{20}$ | $V_{21}$ | $V_{22}$ | CLN AIR PMP | RNS AIR PMP | STOP COCK MTR | CLN SYR PMP | RNS SYR PMP |
| 25.13 Venting lines | - | - | 0 | 0 | 0 | 0 | - | - | on | on | off | off | off |
| 25.14 Disconnect cassette attach cap and reconnect | - | - | 0 | 0 | 0 | 0 | - | - | on | on | off | off | off |
| 25.15 Pressurizing the cassette | - | - | - | 0 | 0 | - | - | 0 | on | on | off | off | off |
| 25.16 Vent lines | - | - | - | 0 | 0 | 0 | - | - | on | on | off | off | off |
| 25.17 Pressurization completed | - | - | - | 0 | 0 | - | - | - | off | off | off | off | off |